US012376877B2

(12) United States Patent
Miyazaki

(10) Patent No.: US 12,376,877 B2
(45) Date of Patent: Aug. 5, 2025

(54) TREATMENT DEVICE

(71) Applicant: OLYMPUS MEDICAL SYSTEMS CORP., Tokyo (JP)

(72) Inventor: Akira Miyazaki, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 849 days.

(21) Appl. No.: 17/527,497

(22) Filed: Nov. 16, 2021

(65) Prior Publication Data

US 2022/0240973 A1 Aug. 4, 2022

Related U.S. Application Data

(60) Provisional application No. 63/144,167, filed on Feb. 1, 2021.

(51) Int. Cl.
*A61B 17/32* (2006.01)
*A61B 17/00* (2006.01)

(52) U.S. Cl.
CPC ............ *A61B 17/320092* (2013.01); *A61B 2017/00367* (2013.01); *A61B 2017/00402* (2013.01); *A61B 2017/00438* (2013.01); *A61B 2017/0046* (2013.01); *A61B 2017/320074* (2017.08); *A61B 2017/320094* (2017.08)

(58) Field of Classification Search
CPC .......... A61B 17/320092; A61B 2017/320094; A61B 2017/320074; A61B 2017/00367; A61B 2017/00402; A61B 2017/00438; A61B 2017/0046
See application file for complete search history.

(56) References Cited

U.S. PATENT DOCUMENTS

| 2007/0282332 A1 | 12/2007 | Witt et al. |
| 2007/0282333 A1 | 12/2007 | Fortson et al. |
| 2007/0282334 A1 | 12/2007 | Young et al. |
| 2007/0282335 A1 | 12/2007 | Young et al. |
| 2012/0253373 A1 | 10/2012 | Young et al. |

(Continued)

FOREIGN PATENT DOCUMENTS

| CN | 101495050 A | 7/2009 |
| CN | 201939397 U | 8/2011 |

OTHER PUBLICATIONS

Office Action dated Apr. 17, 2025, issued in corresponding Chinese Patent Application No. 202210094948.2.

*Primary Examiner* — Ashley L Fishback
(74) *Attorney, Agent, or Firm* — Morgan, Lewis & Bockius LLP

(57) ABSTRACT

A treatment device having a vibration source, a transmission rod, treatment blade, and a jaw piece attached to a movable handle is disclosed. The treatment device is equipped with ultrasonic transducers which includes piezoelectric elements converting electrical power into ultrasonic vibrations. The ultrasonic vibrations are transmitted along the transmission members to the treatment blade that vibrates at ultrasonic frequencies to cut and/or seal tissues. The jaw piece is connected to the movable handle and open and closes with the movement of the movable handle. The treatment device is also equipped with an extension protruding from the operation body that allows the operator to operate the device and the movable handle at ease, even when the device is operated at different angles.

20 Claims, 11 Drawing Sheets

(56) References Cited

U.S. PATENT DOCUMENTS

| | | |
|---|---|---|
| 2013/0338691 A1 | 12/2013 | Young et al. |
| 2015/0245849 A1 | 9/2015 | Young et al. |
| 2018/0132926 A1 | 5/2018 | Asher et al. |
| 2020/0015801 A1* | 1/2020 | Sauer .................... A61B 17/02 |

* cited by examiner

TREATMENT DEVICE

RELATED APPLICATION DATA

This application is based on and claims priority under 35 U.S.C. § 119 to U.S. Provisional Application No. 63/144,167, filed Feb. 1, 2021, the entire contents of which are incorporated herein by reference.

FIELD OF DISCLOSURE

The present disclosure relates to a treatment device having a scissors like structure. The treatment device is equipped with ultrasonic transducer including piezoelectric elements converting electrical power into ultrasonic vibrations. The ultrasonic vibrations and high frequency currents are transmitted along the transmission rod covered by a sheath. A movable handle including a jaw piece is attached to the sheath for clasping tissues to be treated. The sheath, movable handle, and the jaw piece together consist a scissors like structure to be operated by the operator during the treatment procedure.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

FIG. 6 is a figure of a treatment device disclosed in the related art (United States Patent Application Publication No. 2018/0132926A1). The related art surgical instrument 10 includes a plug 11 connected to a generator 5, first modular assembly 100, a second modular assembly 200, and a coupling member 300 that selectively attaches the first modular assembly 100 with second modular assembly 200 in order to form an end effector 12. The first modular assembly 100 includes a handle assembly 110, a shaft assembly 130, and an ultrasonic blade 150. Handle assembly 110 includes a body 112, a finger grip ring 124, and a pair of buttons 126 selectively activating an ultrasonic transducer assembly housed within body 112. Protrusions 136 and 238 are configured to pivotally couple the first modular assembly 100 with coupling member 300. Second modular assembly 200 includes a clamp arm assembly 210, a clamp pad assembly 220, and a distal outer sheath 230. Clamp arm assembly 210 includes an elongated arm 212 and a thumb grip ring 214 and is coupled to distal outer sheath 230 via pins 202. Thumb grip ring 214 and elongated arm 212 together provide a scissor grip type configuration in combination with body 112 and finger grip ring 124. Clamp pad assembly 220 includes a clamp pad 222 facing ultrasonic blade 150, a pair of tissue stops 223 located adjacent to ultrasonic blade 150 and proximal to clamp pad 222, and an arm 224. Distal outer sheath 230 includes a U-shaped body 232 extending from a distal face 235 and defining a longitudinal pathway 236 and a plurality of bores 240. The coupling member 300 comprises a body 302, a pair of resilient arms 304 extending from body 302, and a pair of grips 305 extending from body 302. Resilient arms 304 each define a respective pivot bore 306 and locking assembly 308.

A drawback of the related art treatment device is that scissor grip type configuration using thumb grip ring 214 and finger grip ring 124 implies usage in which the second modular assembly 200 is placed over the first modular assembly 100 and does not accommodate effective usage where the operator twists the surgical instrument 10, such as by orienting the surgical instrument 10 at 180 degree rotation, i.e., upside down. In practice, upon twisting the surgical instrument 10 such as twisting to an upside down orientation, the operator tends to pull out the fingers from the thumb grip ring 214 and finger grip ring 124 and insert the thumb into the finger grip ring 124 and other fingers into the thumb grip ring 214 in order to perform the clumping or peeling operation. Because the thumb grip ring thumb grip ring 214 and finger grip ring 124 are not configured to adapt to such usage, the usability of the surgical instrument 10 is reduced and precision may be negatively impacted.

SUMMARY

Accordingly, there is a need for designing a treatment device with an improved usability in view of the practical usage of the treatment device, including at various orientations and degrees of rotation and particularly at 180 degrees of rotation, which would substantially obviate one or more of the issues due to limitations and disadvantages of related art treatment device.

An object of the present disclosure is to provide an improved treatment device that provides an efficient design for the associated usability compared to the related art. At least one or some of the objectives is achieved by the treatment device disclosed herein.

Additional features and advantages will be set forth in the description that follows, and in part will be apparent from the description, or may be learned by practice of the invention. The objectives and other advantages of the disclosed treatment device will be realized and attained by the structure particularly pointed out in the written description and claims thereof, as well as the appended drawings.

Embodiments of the disclosed treatment device comprises a treatment device comprised of a base handle including an ultrasonic transducer located inside a housing, a transmission rod with a proximal end and a distal end connecting the base handle at the proximal end configured to transmit energy produced by the ultrasonic transducer, treatment blade at the distal end of the transmission rod, a sheath covering the transmission rod, a movable handle connected to the sheath including a jaw piece, an operation body formed between the base handle and the sheath including an operation button, and an extension protruding from the operation body having an extension base and an extension distal end. The bearing surface portion of the movable handle is located on a first side and the extension is located on a second side of the operation body, the first side of the operation body being opposite the second side of the operation body.

Embodiments of the disclosed treatment device further comprises a treatment device wherein an angle formed by a longitudinal axis of the treatment device and an imaginary line connecting a location of a connection portion of the movable handle on the longitudinal axis A and the extension distal end is between 20 and 45 degrees.

Embodiments of the disclosed treatment device further comprises a treatment device wherein the extension has an opening formed between the extension base and the extension distal end, wherein the opening has a depth, and wherein the depth has a distance of 1 to 2.5 cm.

Embodiments of the disclosed treatment device further comprises a treatment device wherein a position of the extension protruding from the operation body is equal to or greater than ±150 degrees from a position of the movable handle, where the positions are taken relative to the longitudinal axis and as seen in a direction down the longitudinal axis.

Embodiments of the disclosed treatment device further comprises a treatment device wherein a distance from a longitudinal axis of the treatment device to the operation body and the base handle at a juncture where the operation body and the base handle are joined together is equal to or less than 5 mm.

Embodiments of the disclosed treatment device further comprises a treatment device wherein the operation body includes a track supporting movement of the moving handle.

Embodiments of the disclosed treatment device further comprises a treatment device wherein the operation body includes more than one operation button.

Embodiments of the disclosed treatment device further comprises a treatment device wherein the movable handle includes an inward bearing surface and an outward bearing surface.

Embodiments of the disclosed treatment device further comprises a treatment device wherein the movable handle has a closed geometry.

Embodiments of the disclosed treatment device further comprises a treatment device wherein the finger ring fits only a single digit of a hand.

Embodiments of the disclosed treatment device further comprises a treatment device wherein the inward bearing surface and the outward bearing surface form part of an inner diameter surface of a finger ring having a closed geometry.

Embodiments of the disclosed treatment device further comprises a treatment device wherein the base handle, transmission rod, treatment blade, and the jaw piece are compatible for use under high frequency treatment.

Embodiments of the disclosed treatment device further comprises a treatment device wherein the base handle includes anti-slipping protrusions.

Embodiments of the disclosed treatment device further comprises a treatment device wherein the base handle is removable from the operation body.

Embodiments of the disclosed treatment device further comprises a treatment device wherein the base handle is joined together with the operation body using a fastener.

Embodiments of the disclosed treatment device further comprises a treatment device wherein the base handle is joined together with the operation body using a leaf spring.

Embodiments of the disclosed treatment device further comprises a treatment device comprised of a base handle including an ultrasonic transducer located inside a housing, a transmission rod with a proximal end and a distal end connected to the base handle at the base handle configured to transmit energy produced by the ultrasonic transducer, a treatment blade at the distal end of the transmission rod, a sheath covering the transmission rod, a movable handle connected to the sheath including a jaw piece, an operation body formed between the base handle and the sheath including an operation button, and an extension protruding from the operation body having an extension base and an extension distal end. The bearing surface portion of the movable handle is located on a first side of the operation body and the extension is located on a second side of the operation body, the first side of the operation body being opposite the second side of the operation body. An angle formed by a longitudinal axis of the treatment device and an imaginary line connecting a location of a connection portion of the movable handle on the longitudinal axis and the extension distal end is between 20 and 45 degrees. The said extension has an opening formed between the extension base and the extension distal end, wherein the opening has a depth, and wherein the depth has a distance of 1 to 2.5 cm. The position of the extension protruding from the operation body is equal to or greater than ±150 degrees from a position of the movable handle, where the positions are taken relative to the longitudinal axis and as seen in a direction down the longitudinal axis.

Embodiments of the disclosed treatment device further comprises a treatment device wherein the movable handle includes an inward bearing surface and an outward bearing surface, and the inward bearing surface and the outward bearing surface form part of an inner diameter surface of a finger ring having a closed geometry.

Other systems, methods, features and advantages will be, or will become, apparent to one with skill in the art upon examination of the following figures and detailed description. It is intended that all such additional systems, methods, features and advantages be included within this description, be within the scope of the present disclosure, and be protected by the following claims. Nothing in this section should be taken as a limitation on those claims. Further aspects and advantages are discussed below in conjunction with the embodiments of the disclosed input device. It is to be understood that both the foregoing general description and the following detailed description of the disclosed input device are examples and explanatory and are intended to provide further explanation of the disclosed input device as claimed.

BRIEF DESCRIPTION OF THE DRAWING

The following detailed description of preferred embodiments can be read in connection with the accompanying drawings in which like numerals designate like elements and in which.

Figure 1A:
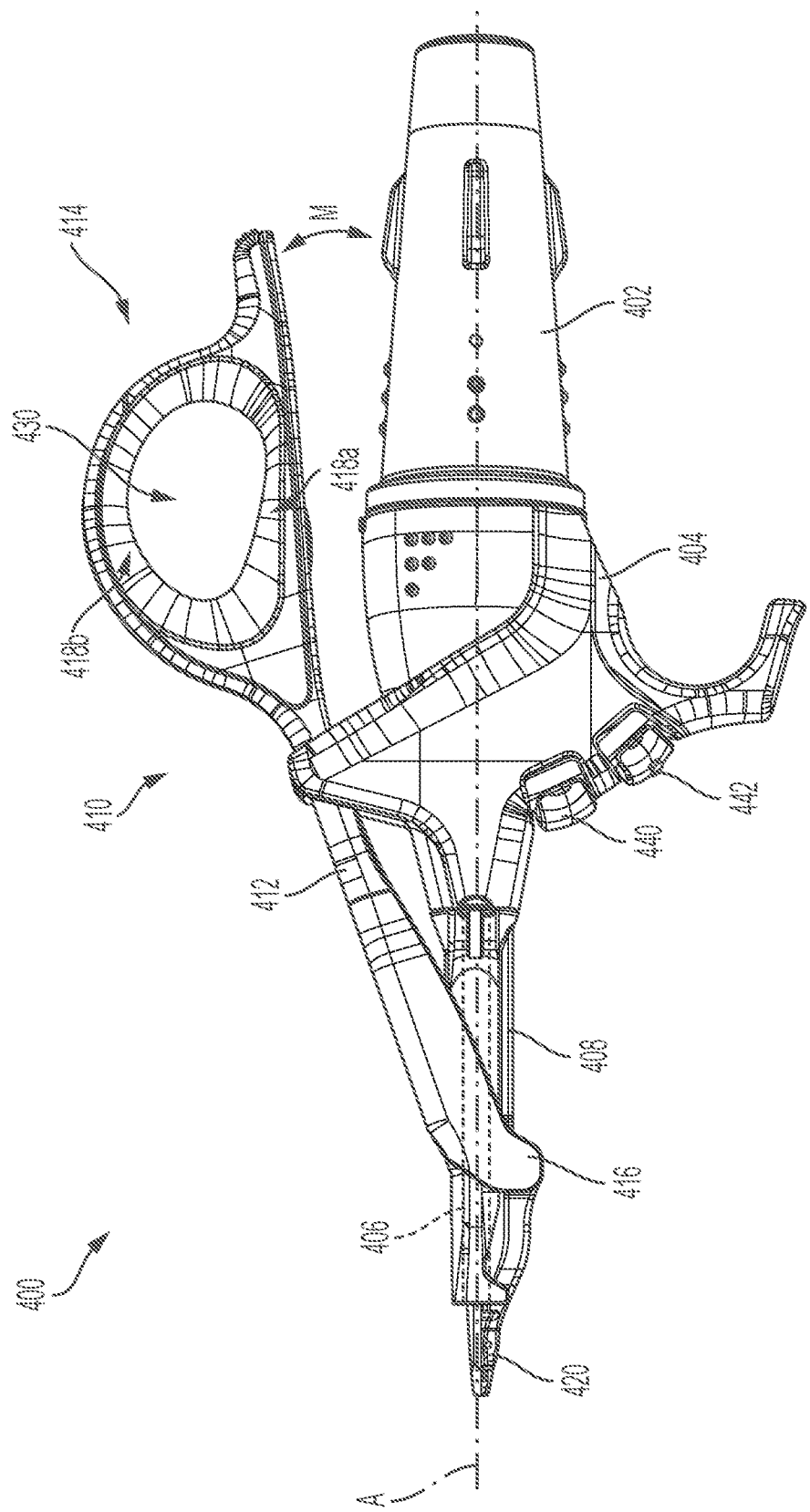
FIG. 1A illustrates a treatment device that includes a base handle, a sheath, a movable handle with a bearing surface in the form of a finger ring, and a jaw piece according to an embodiment of the present disclosure.

For ease of viewing, in some instances only some of the named features in the figures are labeled with reference numerals.

DETAILED DESCRIPTION

FIG. 1A is an illustration of a treatment device 400 consisting of a base handle 402, an operation body 404, a transmission member such as transmission rod 406 (at least a portion of which is interior to a sheath 408), and a movable handle assembly 410. Overall, the treatment device 400 has a longitudinal orientation, with the base handle 402, operation body 404, and transmission rod 406 interior to sheath 408 arranged in that relative positioning along a longitudinal axis A.

An operator handles and operates the treatment device 400 by engaging the operator's hand with the base handle 402 and the movable handle assembly 410. The base handle 402 is the portion where a first portion of the operator's hand grips the treatment device 400 and the movable handle assembly 410 is the portion where a second portion of the operator's hand is positioned. The first and second portions of the operator's hand can each be one or more digits, but also can include portions of the palm of the hand. The specific portions of the operator's hand that engage with the base handle 402 and with the movable handle assembly 410 can also vary as discussed further herein. The movable handle assembly 410 includes a shank 412 connecting a bearing surface portion 414 with a connection portion 416, which can be a pivot point about which the movable handle assembly 410 pivots. The bearing surface portion 414 includes one or more bearing surfaces 418a, 418b, which is the surface of the bearing surface portion 414 that the operator's hand contacts, for example with the thumb or with a different digit, to move the movable handle assembly 410 relative to the base handle 402 (such movement is illustrated by arrow M in FIG. 1A). Because bearing surface 418a is engaged to cause inward movement of the bearing surface portion 414 in a direction toward the base handle 402, it is also called herein an inward bearing surface; because bearing surface 418b is engaged to cause outward movement of the bearing surface portion 414 in a direction away from the base handle 402, it is also called herein an outward bearing surface.

The base handle 402 is connected to a power source supplying power to the treatment device 400, which can also include high-frequency currents used for high-frequency treatments. The power source can be a wired or wireless power source. Alternatively, the base handle can be rechargeable with a rechargeable power source incorporated into, for example, the housing of the base handle 402. An ultrasonic transducer is included in the housing of the base handle 402 and is operably connected to be powered by the power source. The ultrasonic transducer includes piezoelectric elements converting electrical power into ultrasonic vibrations. The base handle 402 may be embodied as a removable part as further described below.

The ultrasonic vibrations created at the base handle 402 are transmitted along the vibration transmission rod 406, which is covered by sheath 408. At the distal tip of the vibration transmission rod 406, a portion not covered by sheath 408 has or is coupled to a treatment blade, which in operation vibrates at ultrasonic frequencies and is used for conducting medical procedures, such as incision and/or coagulation procedures. The treatment blade may also be used for medical procedures using high-frequency currents and serve as a high-frequency electrode. The treatment blade can take any suitable form known in the art and can be integrally formed with the transmission rod 406 or be a discreet component that is removably attached to the transmission rod 406.

The movable handle 410 includes a jaw portion 420. The arrangement of features on the movable handle 410 is such that the jaw portion 420 is separated from the shank 412 by the connection portion 416. When the movable handle 410 is mounted on the treatment device 400, the jaw portion 420 forms part of a cooperating pair of jaw portions that allow for a scissoring or grasping action at the distal end of the treatment device 400. For example, a cooperating pair of jaw portions can include the jaw portion 420 as a first part and a treatment blade or end effector at the end of the transmission rod 406 as a second part. The movable handle 410 can be manipulated (through movement M) by applying force against the inward bearing surface while gripping the base handle 402. The movement of the movable handle 410 is supported by supporting member 422. The movement of the movable handle 410 is transferred across connection portion 416 (which acts as a fulcrum) to close the jaw portion 420 against the other part of the cooperating pair of jaw portions, e.g., in this example, the treatment blade or end effector. Once a sample, such as a tissue, is clasped by the cooperating pair of jaw portions, a treatment procedure using ultrasonic vibration or high frequency current can be performed. When it is desired to open the jaw portion 420, the operator can remove the force applied against the inward bearing surface and, if the movable handle 410 is biased open by, for example, a spring, the cooperating pair of jaw portions will open as the movable handle 410 moves away from the base handle 402, or the operator can apply a force against the outward bearing surface to move the movable handle 410 away from the base handle 402 and the cooperating pair of jaw portions will open as the movable handle 410 moves away from the base handle 402. Combinations of biased movement and application of force against the outward bearing surface can also be used.

Figure 1B:
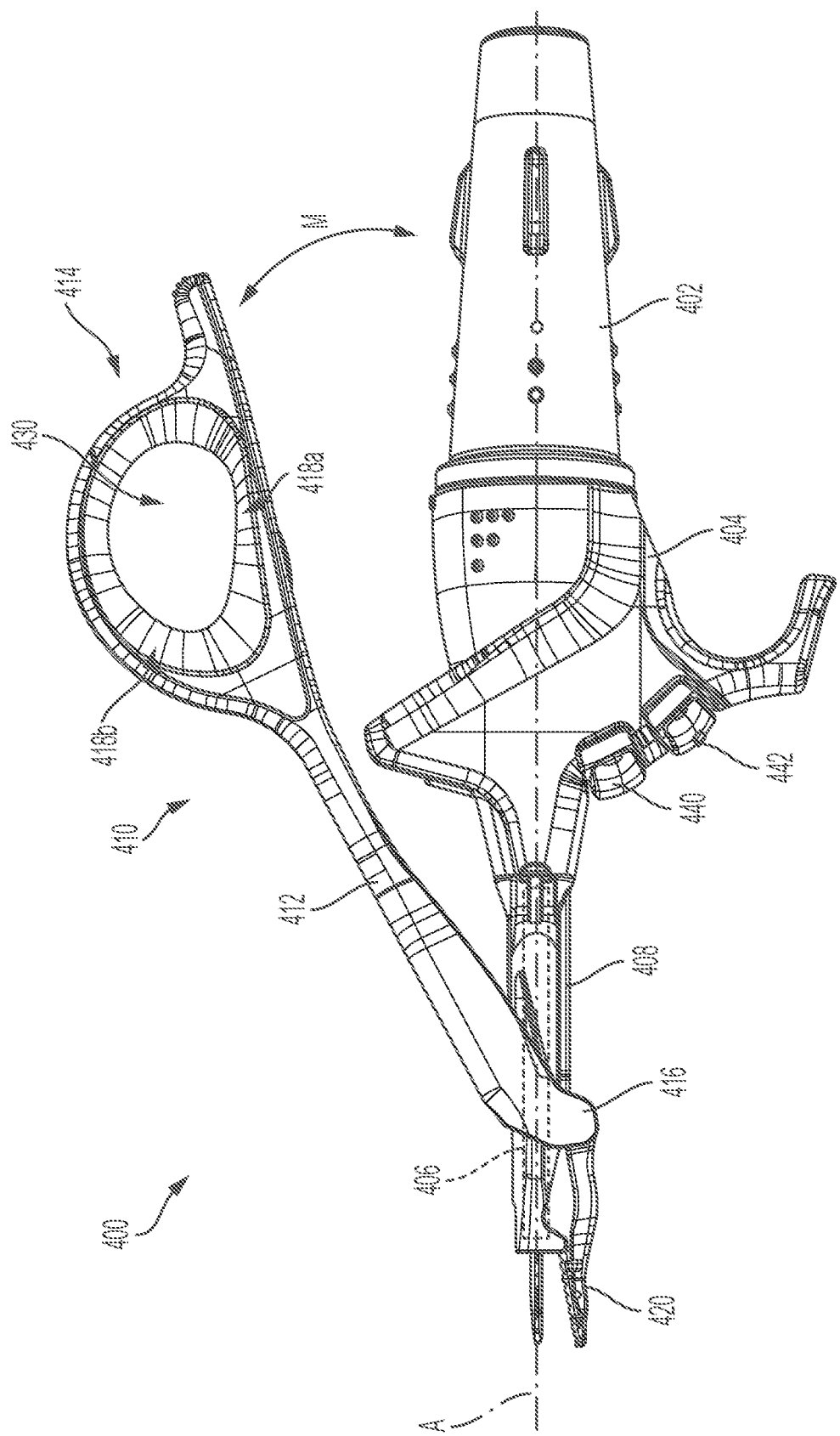
FIG. 1B illustrates a treatment device in FIG. 1A where the movable handle and the jaw piece are in an open position.

FIG. 1B is an illustration of a treatment device 400 as disclosed in FIG. 1A where the movable handle assembly 410 is moved relative to the base handle 402 (movement is illustrated by arrow M in FIG. 1B) in a direction away from the base handle 402. The jaw portion 420 is opened relative to the movement of the movable handle 410 moving away from the base handle 402.

Figure 2:
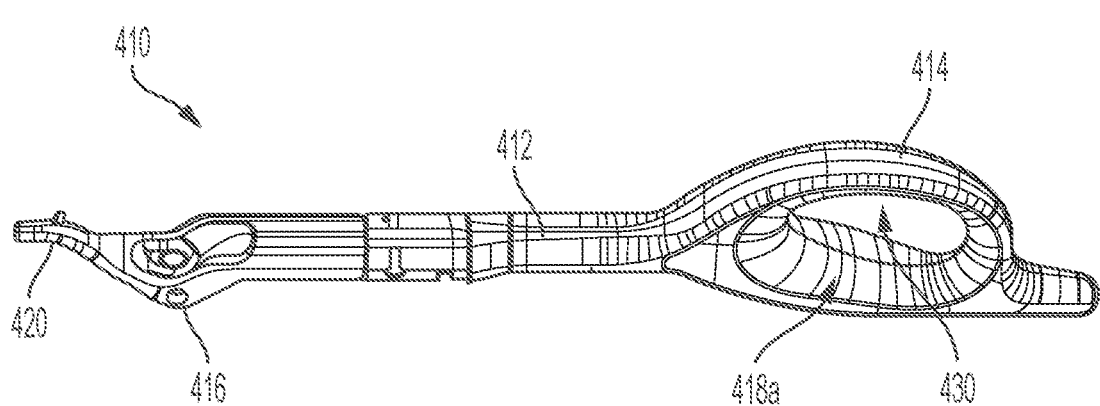
FIG. 2 illustrates the movable handle including the jaw piece disclosed in FIG. 1A.

FIG. 2 is an illustration of the movable handle 410. In the illustrated embodiment, the bearing surface portion 414 is in the form of a closed surface having an inner diameter surface defining an opening 430. The opening 430 may be sized to fit a single digit of a hand or may be designed to fit multiple digits. The connecting portion 416 connects the movable handle to the sheath 408.

Figure 3A:
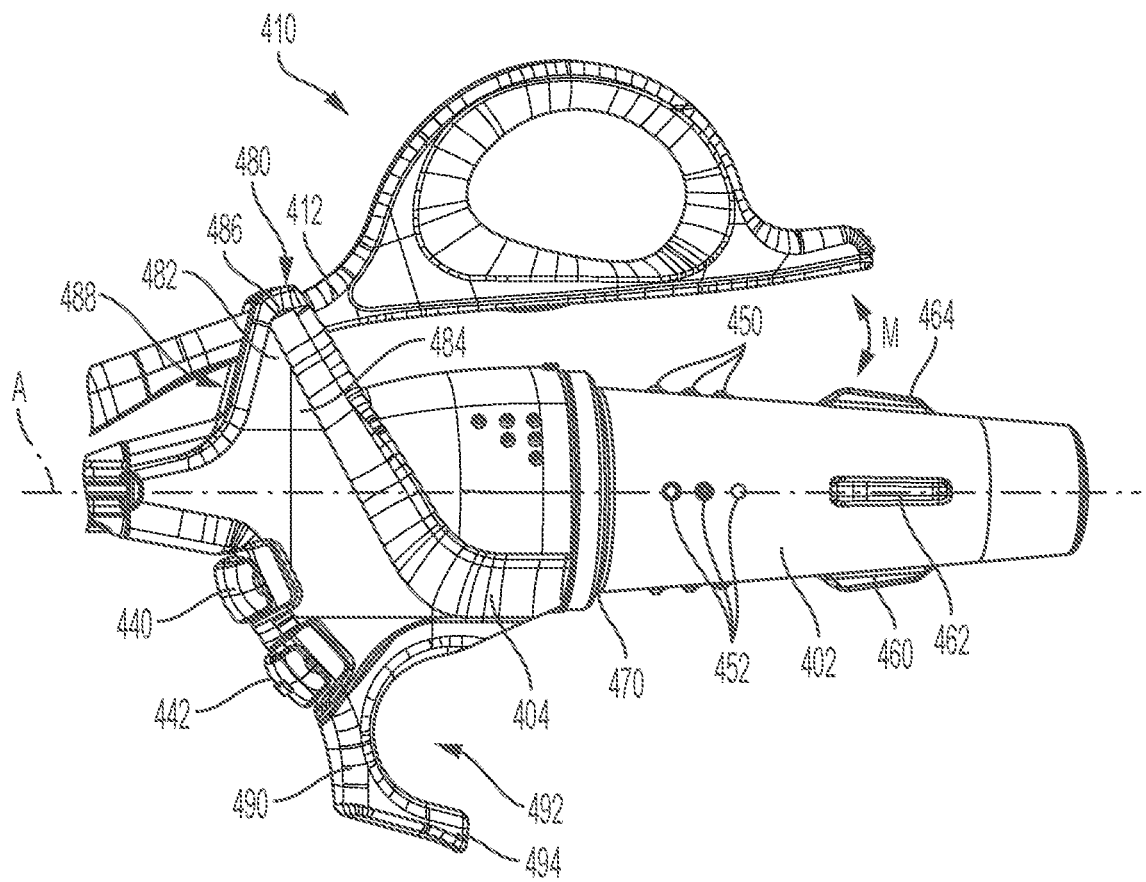
FIG. 3A illustrates a magnified view of a portion of the treatment device and FIG. 3B schematically illustrates a view down the longitudinal axis of the treatment device and showing the relative positions on sides of the body of the treatment device of the movable handle and the protruding extension.

FIG. 3A shows a magnified view of a portion of the treatment device 400. The base handle 402 includes a plurality of protrusions 450, 452 that provide an anti-slipping function and also provides an operator better gripping of the treatment device 400 and base handle 402. The plurality of protrusions 450, 452 can be arranged in groups at one or more locations on the surface of the housing of the base handle 402. A plurality of raised regions 460, 462, 464, which are bulges having an enlarged surface area are also placed for anti-slipping functions and to provide better gripping. Protrusions and raised regions can be used separately or in combination on the medical device 400.

The base handle 402 is connected to operation body 404 at an interface 470 Any discontinuity in height, i.e., radial distance relative to the longitudinal axis A, between the base handle 402 and the operation body 404 at the interface 470 is minimized in order to enable the operator to smoothly change the operator's grip and position of the hand and digits along the surface of the base handle 402 and operation body 404. The base handle 402 may be removable from the operation body 402 in case there is a need to make the remaining portions of the treatment device 400 replaceable in view of sanitary and other purposes. The connection of the base handle 402 and operation body 404 may use connecting features such as fasteners or leaf spring mechanisms, which would allow conductibility between the base handle 402 and operation body 404.

The operation body 404 includes operation buttons 440 and 442, used for actuating ultrasonic vibration transducers, empowering high frequency currents, or other functions of the treatment device 400.

A support member 480 includes two side surfaces 482 that are each connected to the operation body 404 at the base region 484 and are connected to each other at top region 486. The two side surfaces are separated from each other and form sides of a channel 488 in the operation body 404. The shank 412 of the movable handle 410 moves mainly within this channel during movement M of the movable handle 410. The channel helps secure the movable handle 410 to the treatment device 400 and also protects the movable handle 410 from unintended impact. The channel also helps insure a smooth and consistent movement M of the movable handle 410 without any torqueing to one side or the other.

Figure 3B:
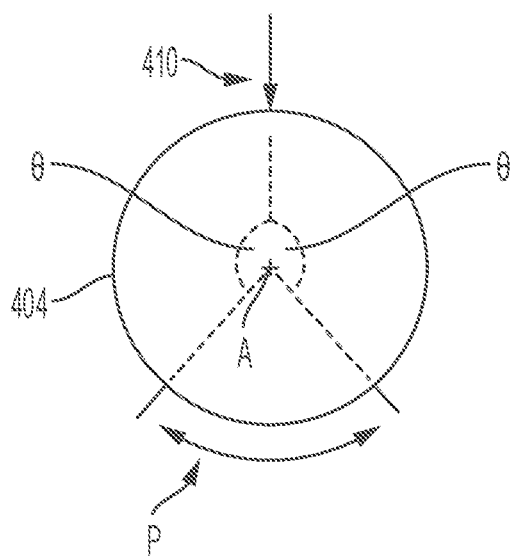

FIG. 3A also illustrates an extension 490 that protrudes from the operation body 404, for example, on a side of the operation body 404 opposite the side on which the bearing surface portion 414 of the movable handle 410 is located. The relative position about the operation body 404 of the movable handle 410 and an arc P representing the range of positions for the extension 490 is shown in FIG. 3B. In example embodiments and as schematically represented in FIG. 3B, the extension 490 protruding from the operation body 404 is located at a position (relative to the position of the moveable handle 410) such that an angle (θ) between the position of the extension 490 and the position of the movable handle 410 that is equal to or greater than ±150 degrees, alternatively equal to or greater than ±165 degrees or equal to or greater than ±175 degrees, where the positions are taken relative to the longitudinal axis A and as seen in a direction down the longitudinal axis A. The extension is curved or angled towards the base handle 404 so that an opening 492 is formed between the extension base and the extension distal end 494. This opening 492 functions to protect the portion of the operator's hand used for gripping the base handle 402 from unintended impact. The opening 492 can also serves as a bearing surface when moving the movable handle 410 during certain usage of the treatment device 400, as further described below.

Figure 4A:
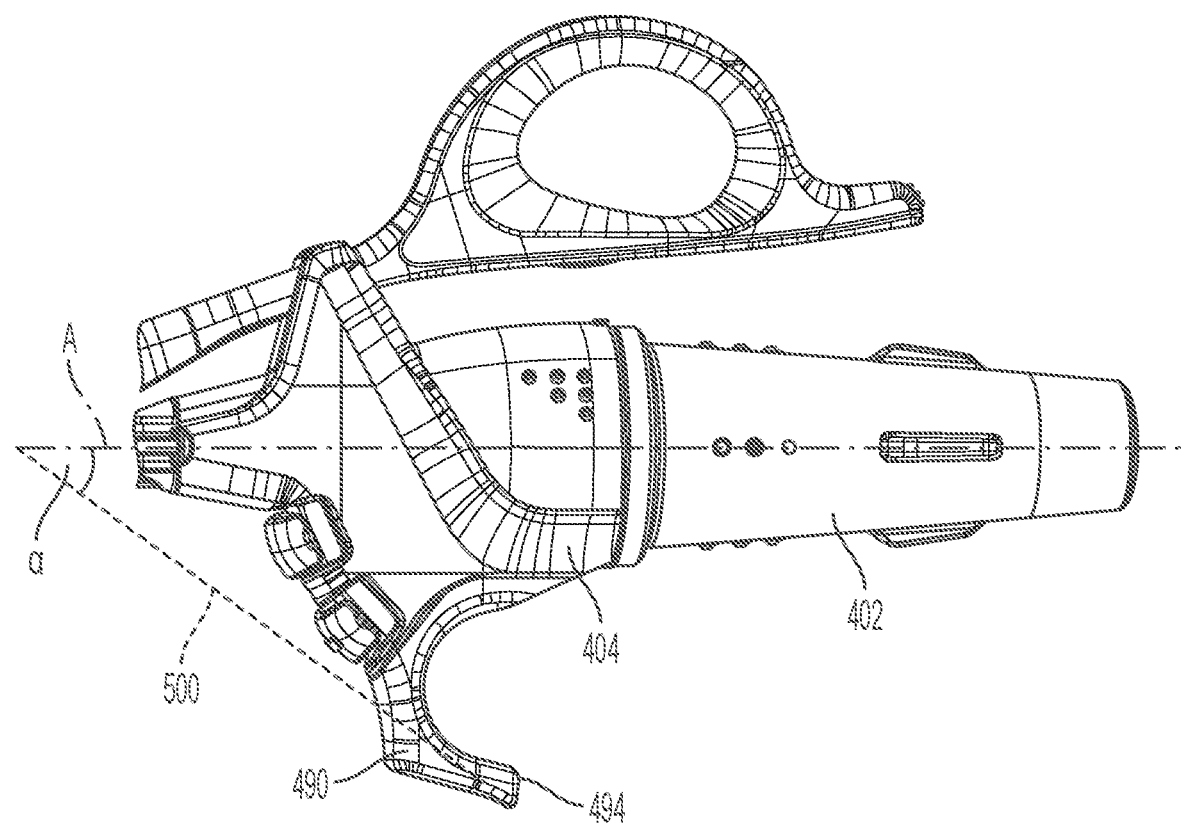
FIGS. 4A and 4B illustrate a magnified view of a portion of the treatment device and indicating locations of certain disclosed measurements.

FIG. 4A is a magnified view of a portion of the treatment device 400 and showing the relationship between the longitudinal axis A of the treatment device 400 and the imaginary auxiliary line 500 connecting the location of the connection portion 416 on the longitudinal axis A and the extension distal end 494. An angle α formed between longitudinal axis A and the imaginary auxiliary line 500 is approximately 33 degrees. The optimal value for angle α is between 20 to 45 degrees for the extension 490 to serve its supporting purposes further described below.

Figure 4B:
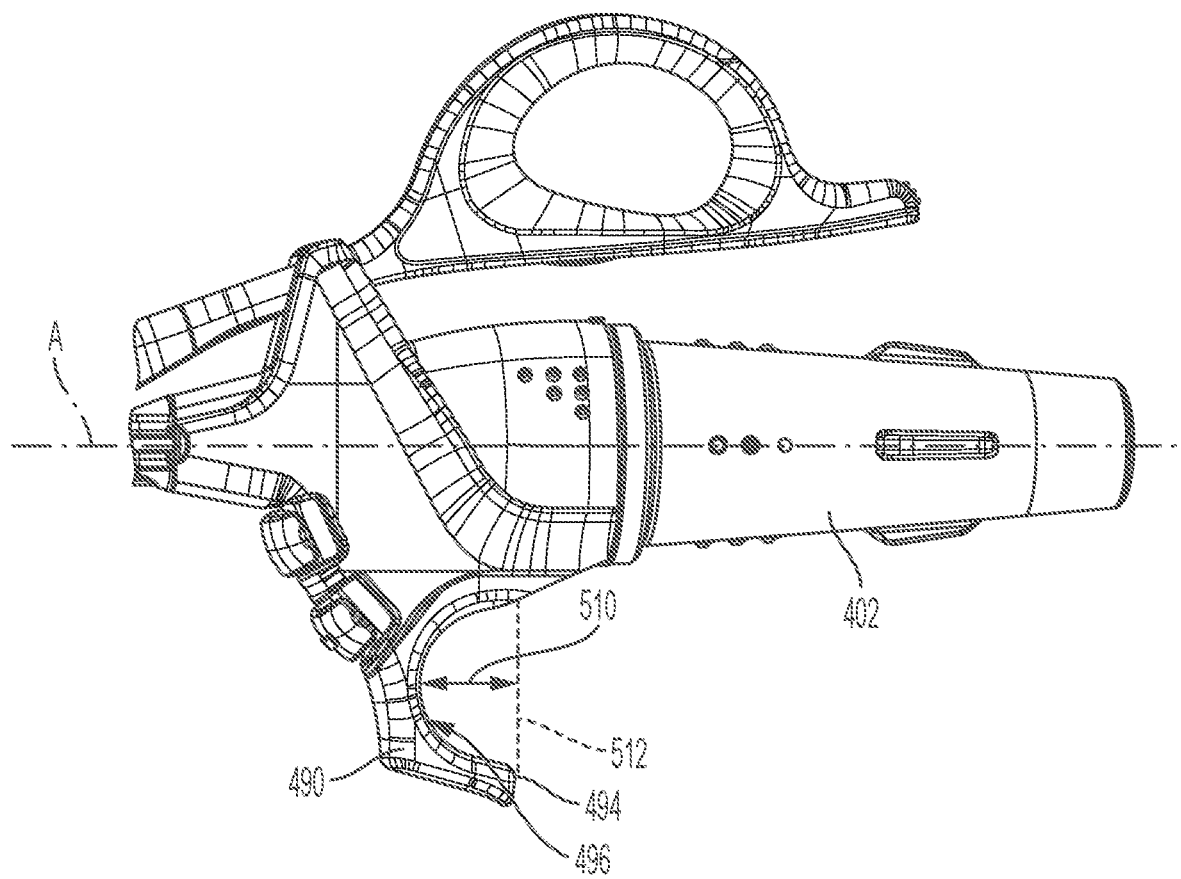

FIG. 4B shows a magnified view of a portion of the treatment device 400 and showing a distance 510, which is the depth of the opening 492. Here, the measurement of the depth of the opening 492 is taken as the largest distance between an imaginary bridge line 512 and an inner surface 496 of the extension 490, where the imaginary bridge line is the imaginary line spanning the opening 492 between the extension distal end 494 and the operation body 404 and that is perpendicular to the longitudinal axis A. In general, the distance 510 is a balance between being too small, such that an operator may have difficulty getting a grip on this portion of the treatment device 400, and being too big, such that the extension 490 may make it difficult for an operator to reposition the grip on this portion of the treatment device 400 after rotating the treatment device 400. As an example, the distance 510 disclosed in FIG. 4B is approximately 1.5 cm and an optimal distance 510 would be between 1 cm to 2.5 cm for the extension 490 to serve its supporting purposes further described below.

Figure 5A:
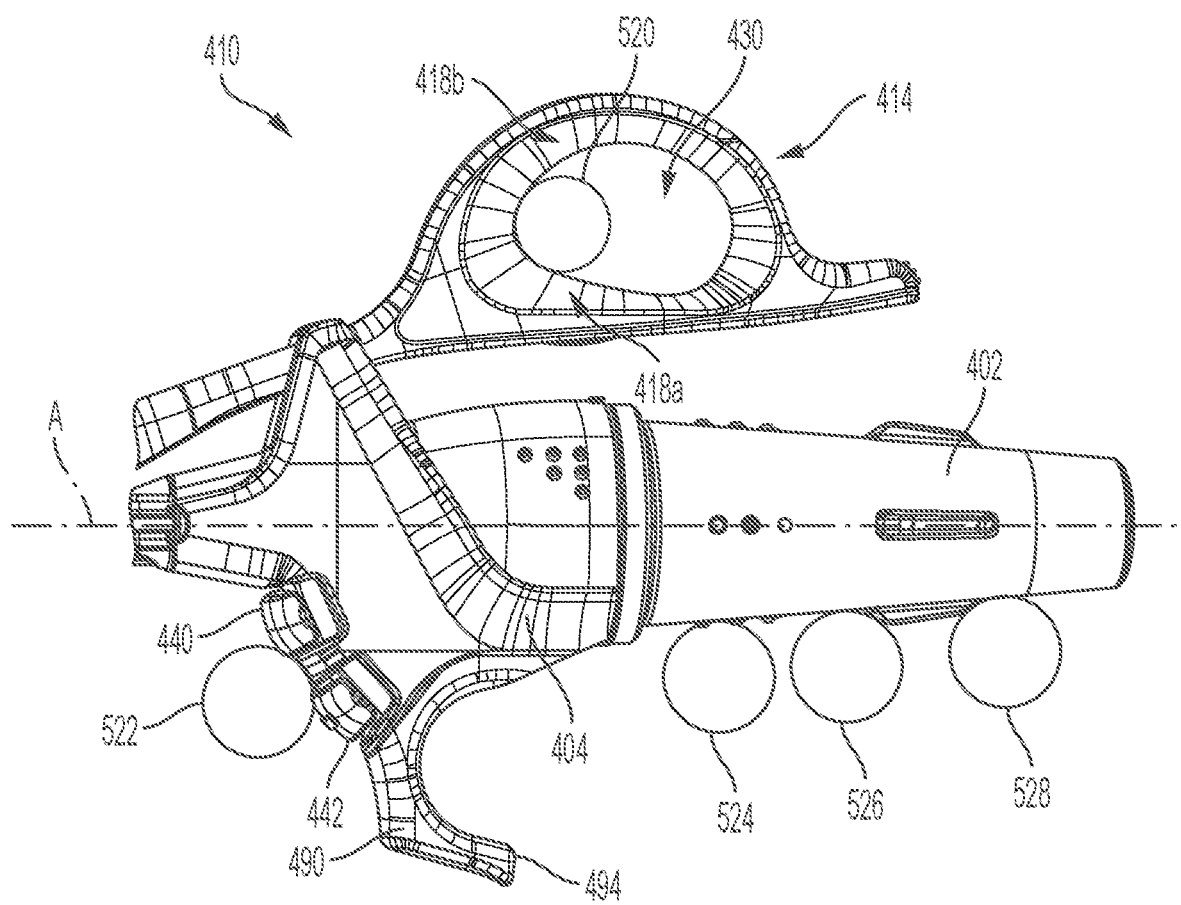
FIGS. 5A to 5D illustrates a magnified view of the treatment device with indication of the location of the operator's fingers.

FIG. 5A shows a magnified view of a portion of the treatment device 400 in which an operator's digits are illustrated as they can, in one embodiment, be placed for using the treatment device 400. In the illustrated embodiment, the operator's digits are illustrated as circles. For example, circle 520 indicates an operator's digit (such as a thumb) placed in opening 430 and contacting at least a portion of the inward bearing surface. One or more other digits of the operator would be placed on or near the operation buttons 440 and 442 for operation of the same, indicated by circle 522. Still other digits of the operator would be placed on the base handle 402, indicated by circles 524, 526, and 528. The digits represented by circles 524, 526, and 528 may be used all together to grip the base handle 402 or portions of the operation body 404, or only one or two of the fingers may be sufficient to provide the necessary grip for the operation of the treatment device 400. In this configuration, the base handle 402 provides sufficient contact and support to the operator's grip so that a force can be applied against the inward bearing surface by the digit indicated by circle 520 to operate the jaw portion 420.

Figure 5B:
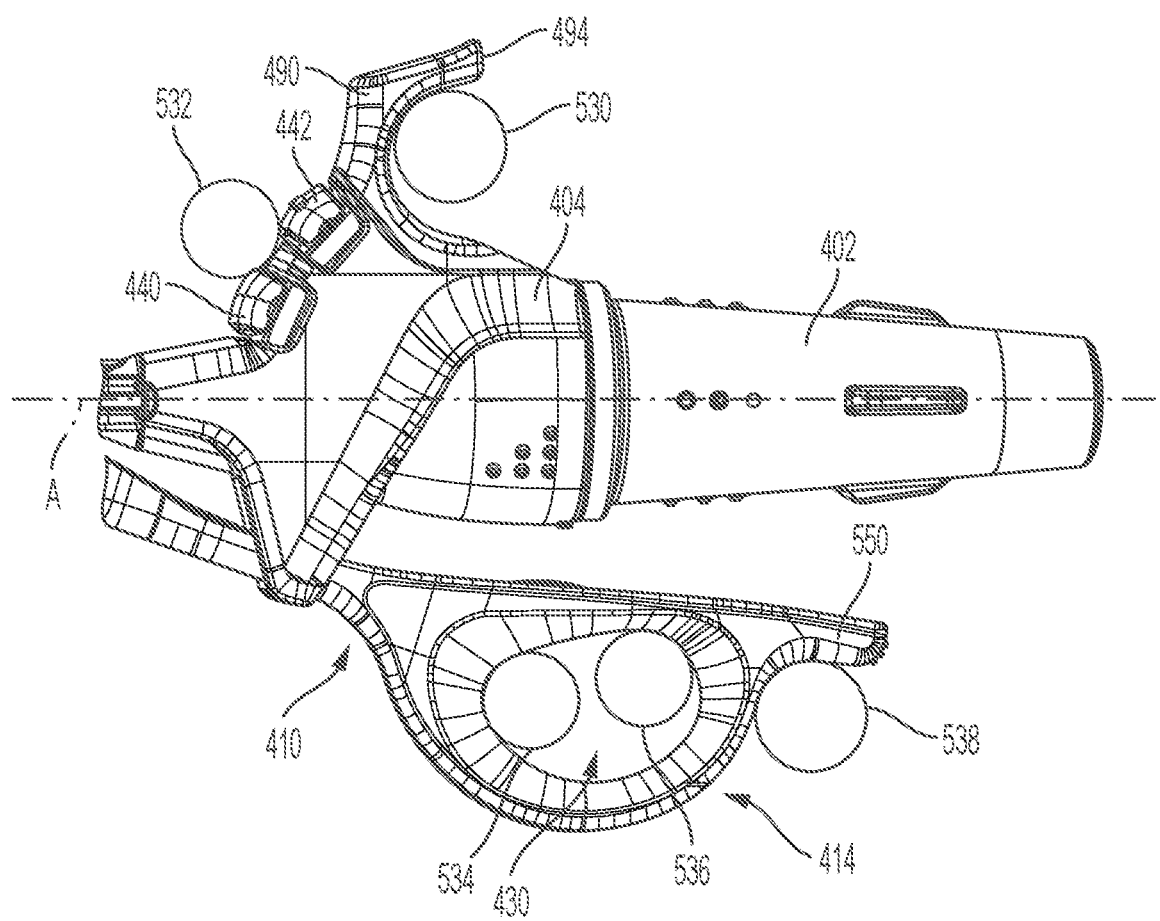

FIG. 5B shows a magnified view of a portion of the treatment device 400 in which an operator's digits are illustrated as they can, in a second embodiment, be placed for using the treatment device 400 where the operator's digits are illustrated as circles. In this second embodiment, the treatment device 400 is rotated 180 degrees relative to the treatment device 400 in the first embodiment illustrated in FIG. 5A. Such rotation (as well as other degrees of rotation) can occur due to physical requirements arising during a treatment procedure. In such an instance, an operator may find it difficult to operate the treatment device with a twisted arm and the operator would change the hold of the treatment device to facilitate use.

Thus, in the second embodiment illustrated in FIG. 5B, an operator can change the placement of digits on the treatment device from that previously illustrated. For example, circle 530 indicates an operator's digit (such as a thumb) placed in opening 492 and contacting at least a portion of the inner surface 496 of extension 490. One or more other digits of the operator would be placed on or near the operation buttons 440 and 442 for operation of the same, indicated by circle 532. Still other digits of the operator would be placed in the opening 430 of the movable handle 410 and contacting at least a portion of the inward bearing surface, indicated by circles 534 and 536. If not also inserted in opening 430, a further digit 538 can be placed outside the opening 430 and in contact with extension 550 of the movable handle.

In this configuration, the extension 490 can be used as a supporting structure to the digit (indicated by circle 530) and provides sufficient contact and support so that the digits (indicated by circles 534, 536) in the opening 430 of the movable handle 410 can be used to apply a force against the inward bearing surface to operate the jaw portion 420. In this embodiment, the extension 490 is especially useful in the case of opening the movable handle 410 by moving the digits away from the longitudinal axis A of the treatment device 400. Also, the further digit 538 may or may not provide force against extension 550 for operating the movable handle 410.

Figure 5C:
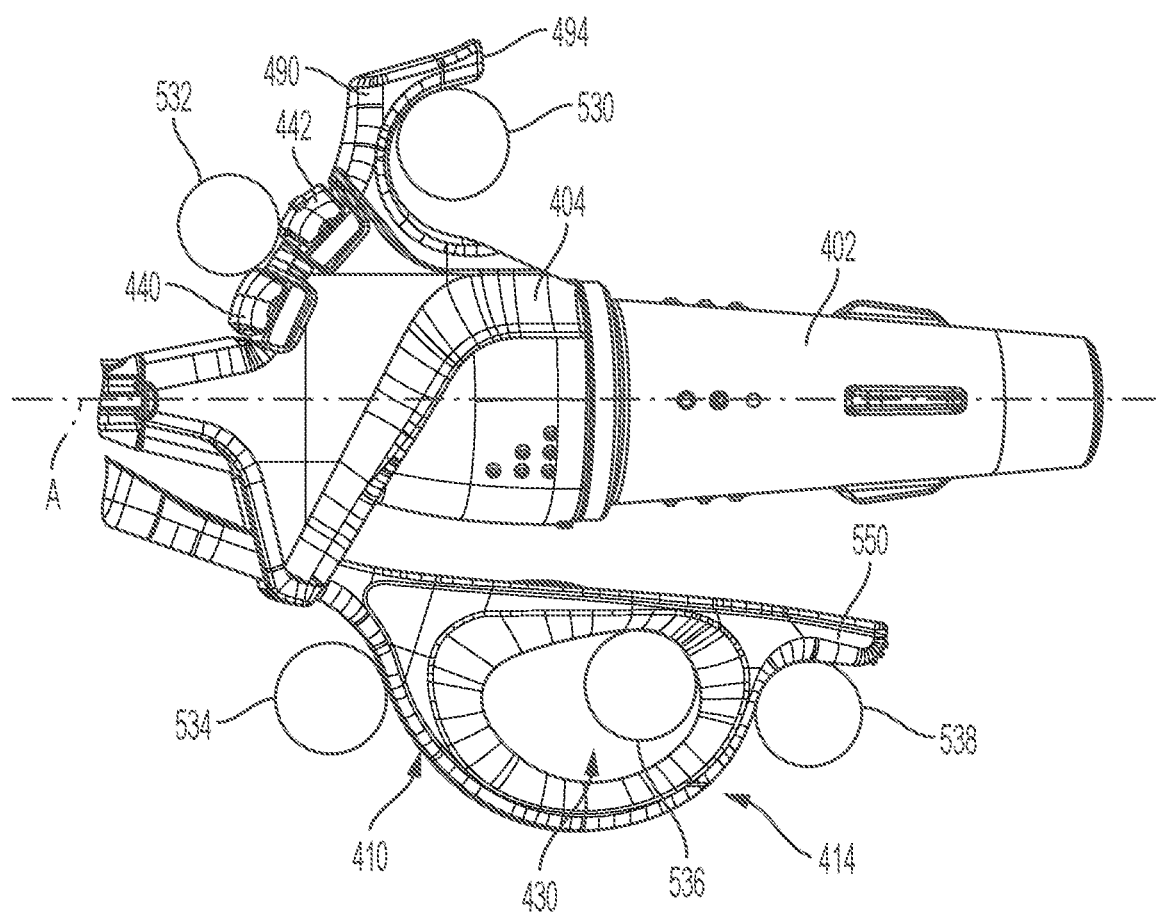
Figure 5D:
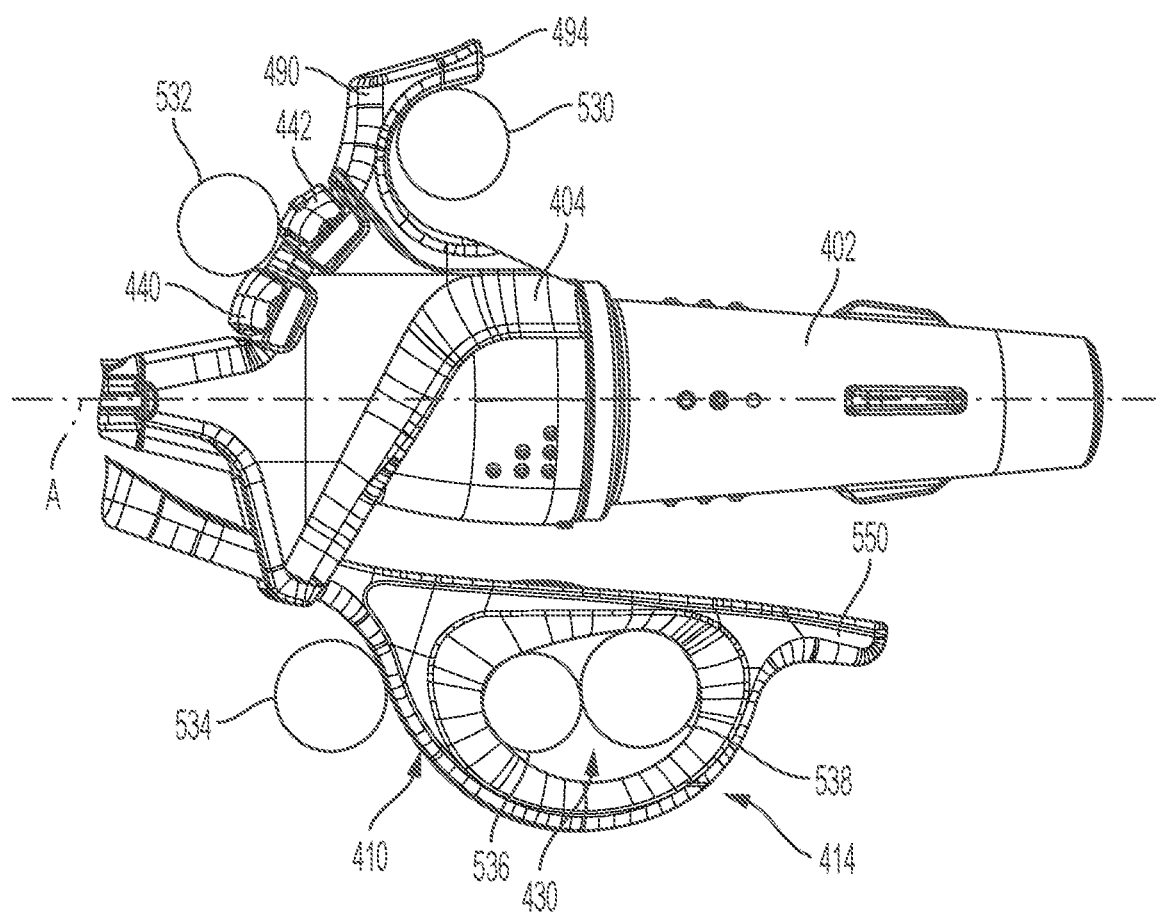
Figure 6:
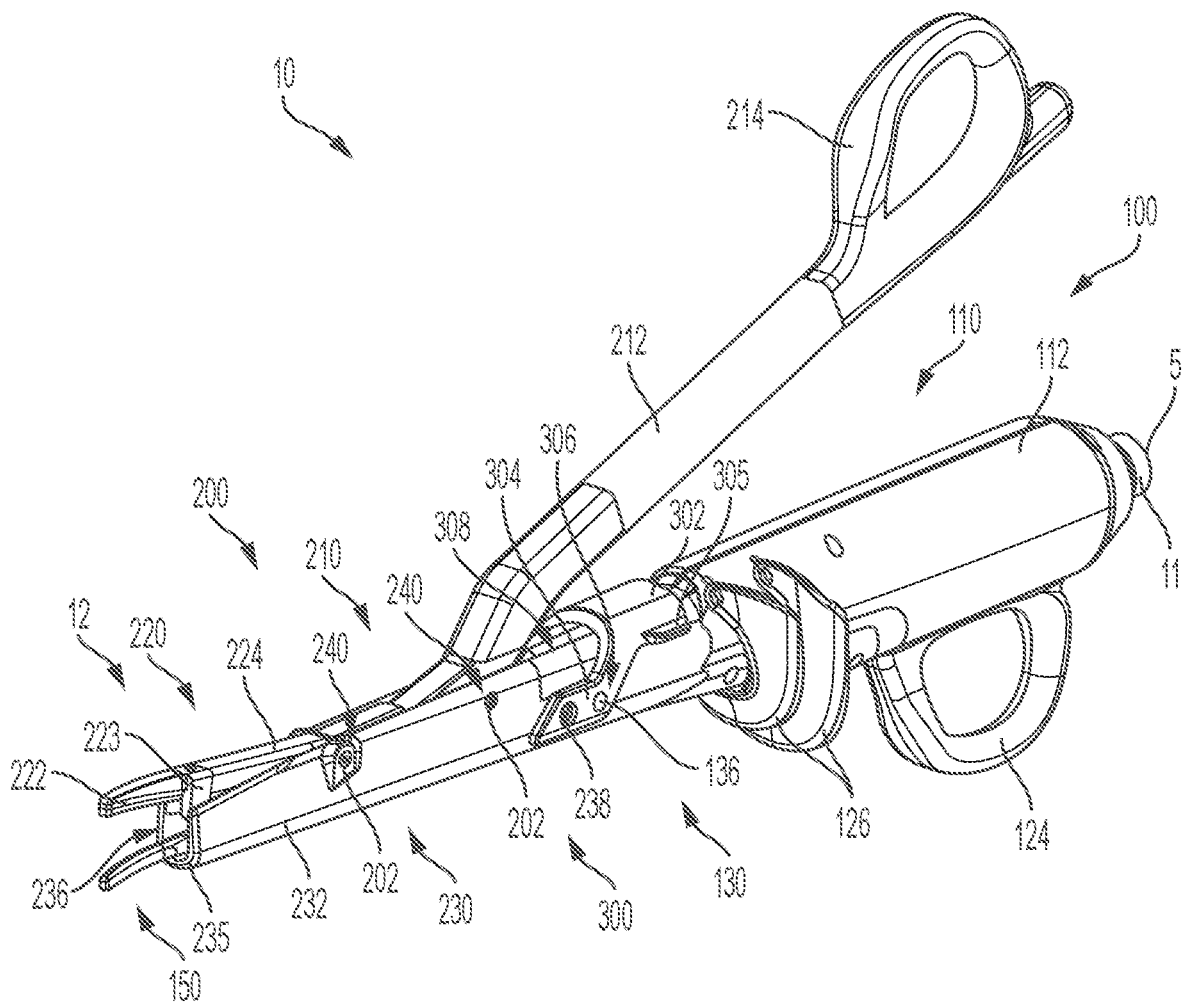
FIG. 6 is a figure from the discussed prior art.

FIGS. 5C and 5D shows a magnified view of a portion of the treatment device 400 in which an operator's digits are illustrated as they can, in a third and fourth embodiment, be placed for using the treatment device 400 where the operator's digits are illustrated as circles. In this third and fourth embodiment, the treatment device 400 is rotated 180 degrees relative to the treatment device 400 in the first embodiment illustrated in FIG. 5A. Such rotation (as well as other degrees of rotation) can occur due to physical requirements arising during a treatment procedure. In such an instance, an operator may find it difficult to operate the treatment device with a twisted arm and the operator would change the hold of the treatment device to facilitate use.

In the third embodiment illustrated in FIG. 5C, the operator places a digit within opening 430 of the movable handle 410 and contacts a portion of the inward bearing surface indicated by circles 536. In the fourth embodiment illustrated in FIG. 5D, the operator places two digits within opening 430 of the movable handle 410 and contacts a portion of the inward bearing surface indicated by circles 536 and 538.

In these configurations, the extension 490 can be used as a supporting structure to the digit (indicated by circle 530) and provides sufficient contact and support so that the digits (indicated by circle 536 in the third embodiment and 536 and 538 in the fourth embodiment) in the opening 430 of the movable handle 410 can be used to apply a force against the inward bearing surface to operate the jaw portion 420.

Although illustrated by circles, it should be appreciated that the number and placement of digits of an operator may vary while staying within the scope of the disclosed treatment device 400 and its operation.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A treatment device, comprising:
   a base handle including an ultrasonic transducer
   a rod connected to the base handle, wherein the rod is configured to transmit energy produced by the ultrasonic transducer;
   a sheath covering the rod;
   a movable handle connected to the sheath and including a bearing surface;
   an operation body located between the base handle and the sheath and including an operation button; and
   an extension protruding from the operation body, the extension having an extension base and an extension distal end,
   wherein the bearing surface is located opposite the extension relative to the operation body, and
   wherein the base handle is removable from the operation body.

2. The treatment device according to claim 1, further comprising a connection portion connecting the movable handle to the sheath,
   wherein an angle defined by a longitudinal axis of the rod and an imaginary line connecting a location of a connection portion of the movable handle on the longitudinal axis A and the extension distal end is between 20 and 45 degrees.

3. The treatment device according to claim 2, wherein the extension has an opening formed between the extension base and the extension distal end, wherein the opening has a depth, and wherein the depth has a distance of 1 to 2.5 cm.

4. The treatment device according to claim 1, wherein a position of the extension protruding from the operation body is equal to or greater than ±150 degrees from a position of the movable handle, where the positions are taken relative to the longitudinal axis and as seen in a direction down the longitudinal axis.

5. The treatment device according to claim 1, wherein a distance from a longitudinal axis of the rod to the operation body and the base handle at a juncture where the operation body and the base handle are joined together is equal to or less than 5 mm.

6. The treatment device according to claim 1, wherein the operation body includes a track supporting movement of the movable handle.

7. The treatment device according to claim 1, wherein the operation body includes more than one operation button.

8. The treatment device according to claim 1, wherein the movable handle includes an inward bearing surface and an outward bearing surface.

9. The treatment device according to claim 8, wherein the inward bearing surface and the outward bearing surface form part of an inner diameter surface of a finger ring having a closed geometry.

10. The treatment device according to claim 9, wherein the finger ring fits only a single digit of a hand.

11. The treatment device according to claim 1, wherein the movable handle has a closed geometry.

12. The treatment device according to claim 1, wherein the base handle includes anti-slipping protrusions.

13. The treatment device according to claim 1, wherein the base handle is joined together with the operation body using a fastener.

14. The treatment device according to claim 1, wherein the base handle is joined together with the operation body using a leaf spring.

15. The treatment device according to claim 1, further comprising a blade located at a distal end of the rod.

16. The treatment device according to claim 15, further comprising a jaw piece facing the rod,
   wherein the base handle, the rod, the blade, and the jaw piece are compatible for use under high frequency treatment.

17. A treatment device, comprising:
   a base handle including an ultrasonic transducer
   a rod connected to the base handle, wherein the rod is configured to transmit energy produced by the ultrasonic transducer;
   a sheath covering the rod;
   a movable handle connected to the sheath and including a bearing surface;
   an operation body located between the base handle and the sheath and including an operation button and a track supporting movement of the movable handle; and
   an extension protruding from the operation body, the extension having an extension base and an extension distal end,
   wherein the bearing surface is located opposite the extension relative to the operation body.

18. The treatment device according to claim 17, wherein the movable handle includes an inward bearing surface and an outward bearing surface, and
   wherein the inward bearing surface and the outward bearing surface form part of an inner diameter surface of a finger ring having a closed geometry.

19. A treatment device, comprising:
- a base handle including an ultrasonic transducer;
- a rod connected to the base handle;
- a sheath covering the rod;
- a movable handle connected to the sheath; and
- an operation body located between the base handle and the sheath, wherein the operation body is configured so that the base handle can be attached and detached,
- wherein the base handle and the operation body are connected using a leaf spring.

20. The treatment device according to claim 19, wherein the movable handle has an opening, and
- wherein the treatment device is configured so that when the treatment device is gripped by a hand, a thumb is placed in the opening and at least one of the remaining fingers grips the base handle.

* * * * *